United States Patent [19]
Watanabe et al.

[11] Patent Number: 5,379,348
[45] Date of Patent: Jan. 3, 1995

[54] PATTERN DEFECTS INSPECTION SYSTEM

[75] Inventors: Toshiyuki Watanabe; Hideo Tsuchiya, both of Yokohama; Toru Tojo, Kanagawa; Tomohide Watanabe, Yokohama, all of Japan

[73] Assignee: Kabushiki Kaisha Toshiba, Kawasaki, Japan

[21] Appl. No.: 40,852

[22] Filed: Mar. 31, 1993

[30] Foreign Application Priority Data

Mar. 31, 1992 [JP] Japan .................. 4-105673

[51] Int. Cl.$^6$ .................. G06K 9/00; H04N 7/00; G01N 21/00
[52] U.S. Cl. .................. 382/8; 348/126; 356/237
[58] Field of Search .................. 356/237, 394; 382/8; 358/101, 106; 348/86, 87, 125, 126

[56]  References Cited
U.S. PATENT DOCUMENTS

| | | | |
|---|---|---|---|
| 4,809,341 | 2/1989 | Matsui et al. | 382/8 |
| 4,926,489 | 5/1990 | Danielson et al. | 382/8 |
| 5,046,109 | 9/1991 | Fujimori et al. | 382/8 |
| 5,235,400 | 8/1993 | Terasawa et al. | 356/237 |

Primary Examiner—Michael T. Razavi
Assistant Examiner—David Fox
Attorney, Agent, or Firm—Oblon, Spivak, McClelland, Maier, Neustadt

[57] ABSTRACT

A pattern defects inspection system inspects the presence/absence of pattern defects in a photomask as an object to be inspected in which a chromium pattern and a phase shift pattern are formed together. Measurement data output from a sensor circuit for generating measurement pattern data by inspecting measurement patterns corresponding to two types of patterns formed on the object by radiating light on the object, and two identifiable design data stored in a magnetic disk unit in advance, i.e., chromium pattern design data used to form a chromium pattern and phase shift pattern design data used to form a phase shift pattern, are read out by a bit pattern generator for performing development processing. The two types of bit data obtained by the bit pattern generator are synthesized according to the same coordinate definition. The synthesized design data is compared with the measurement data by a comparator. As a result, the presence/absence of pattern defects in the object can be determined.

18 Claims, 13 Drawing Sheets

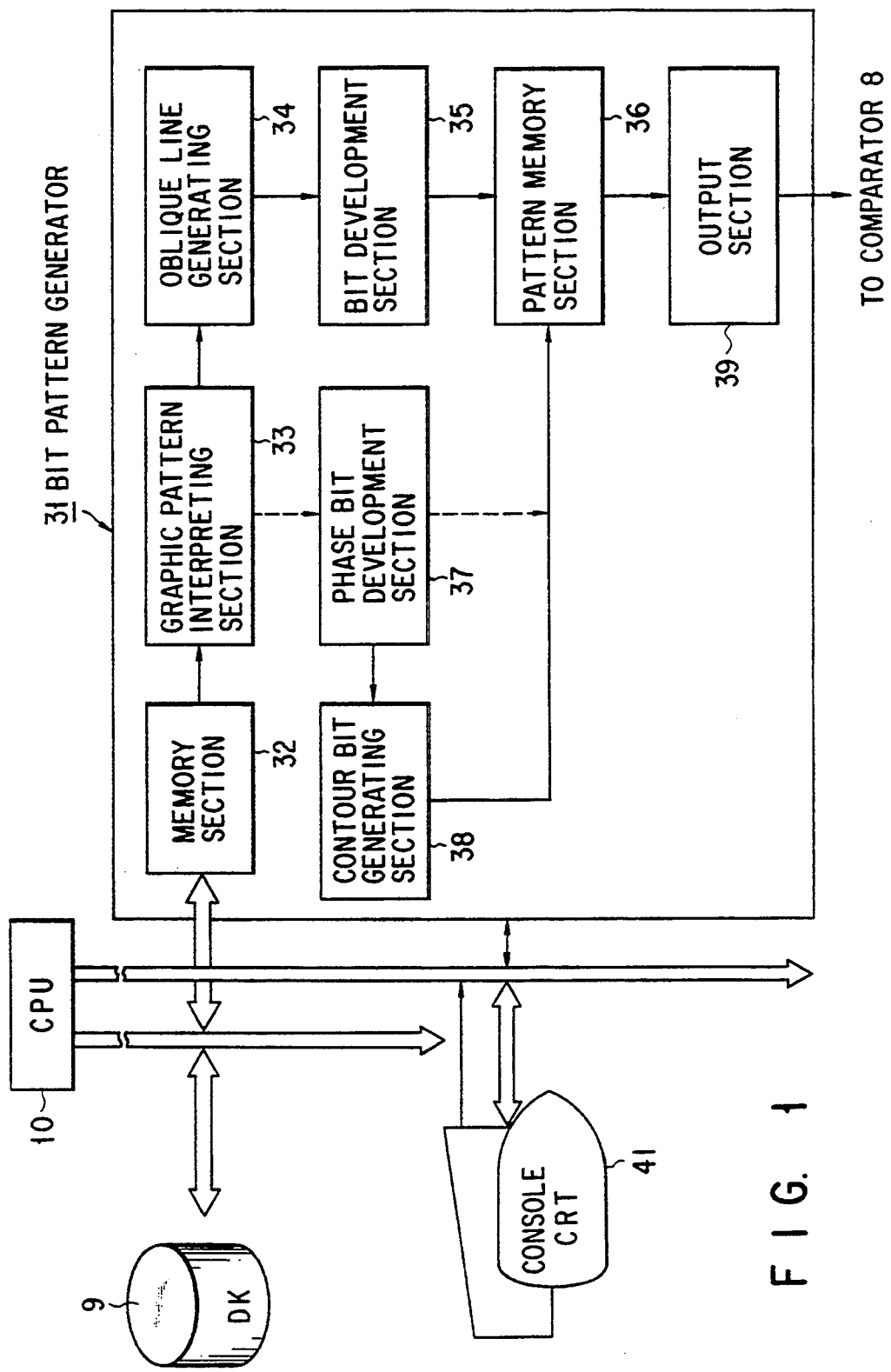

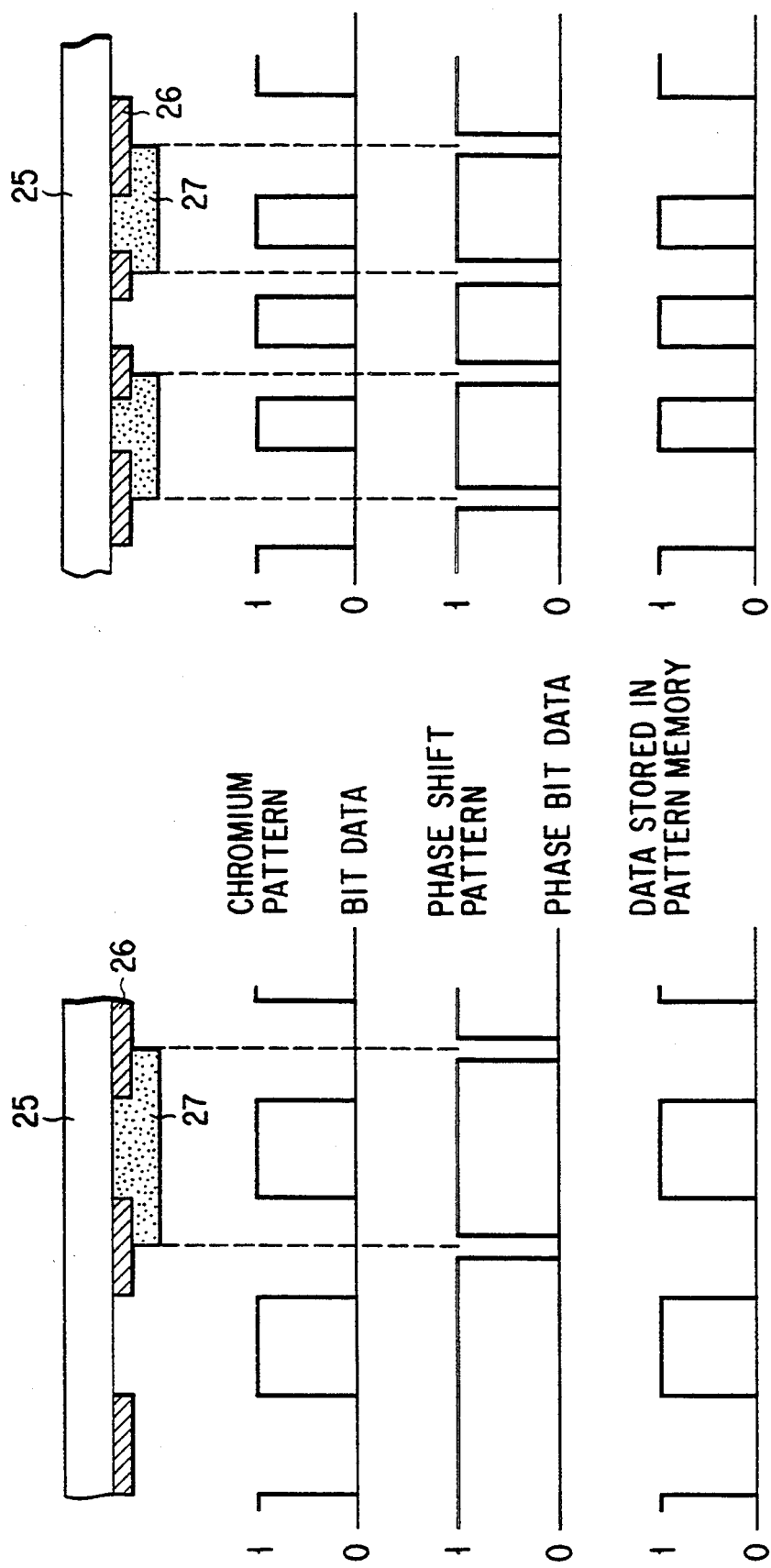

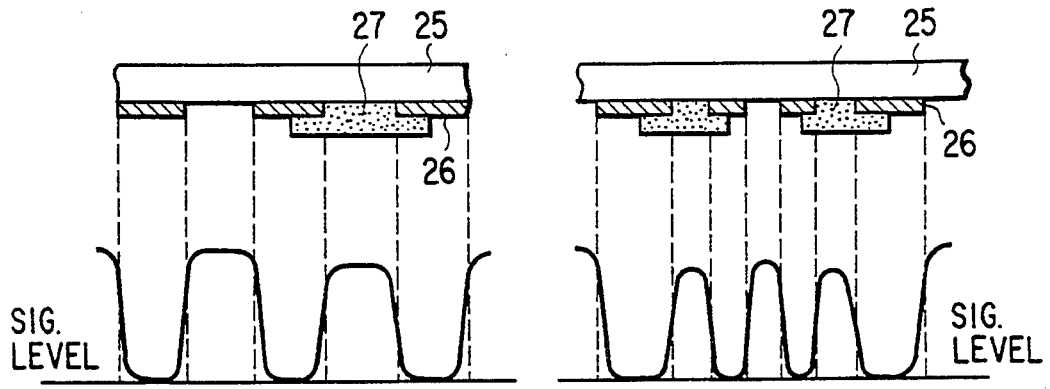
F I G. 6A      F I G. 6B
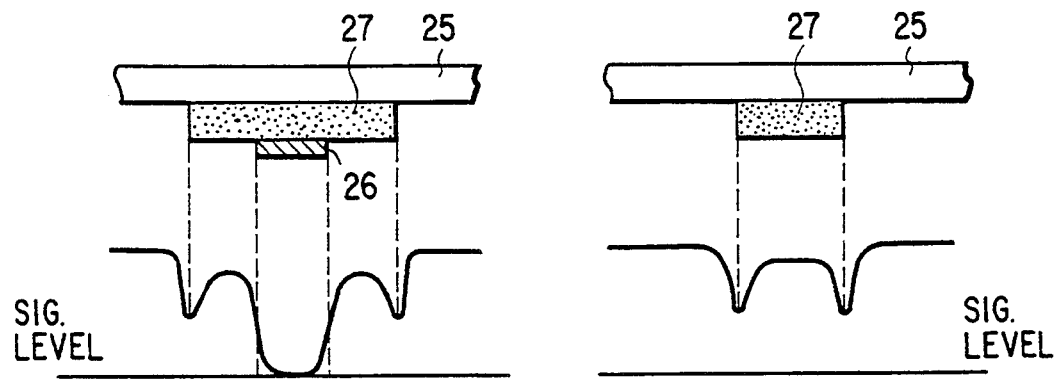
F I G. 6C      F I G. 6D
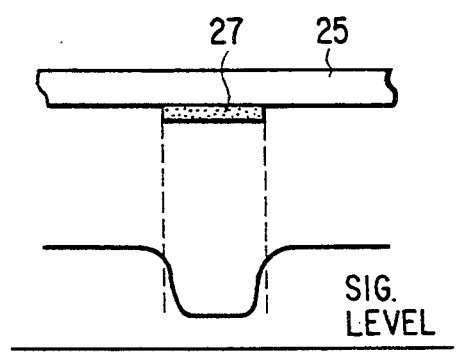
F I G. 6E

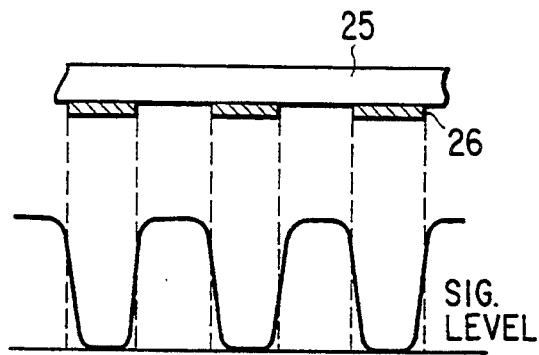
F I G. 7A
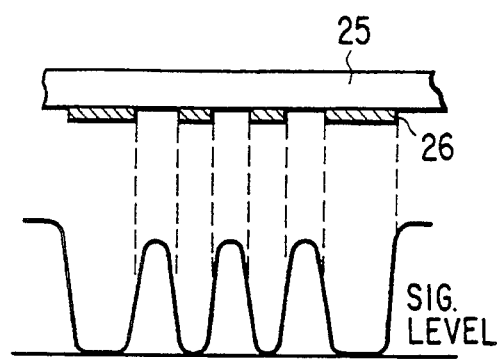
F I G. 7B
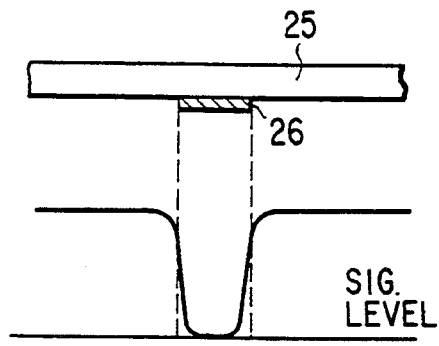
F I G. 7C
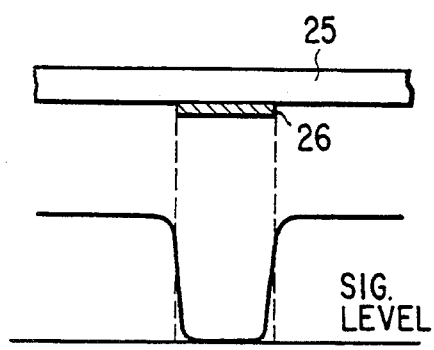
F I G. 7D
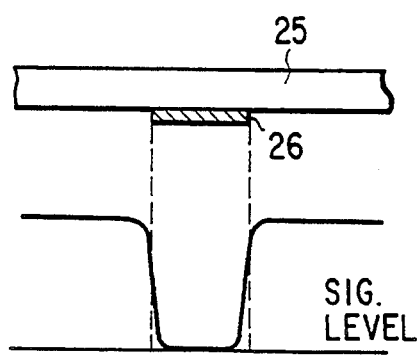
F I G. 7E

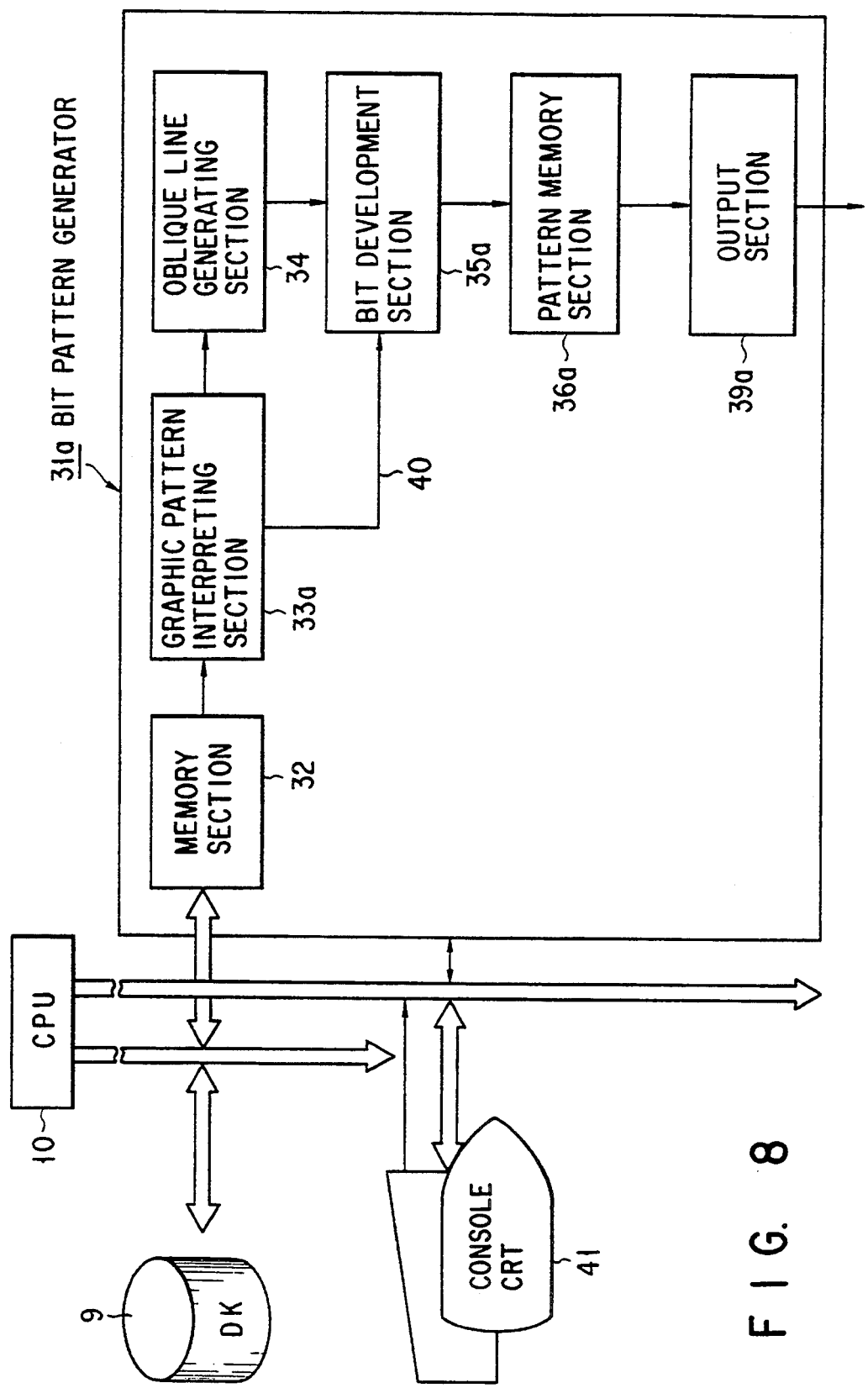
F I G. 8

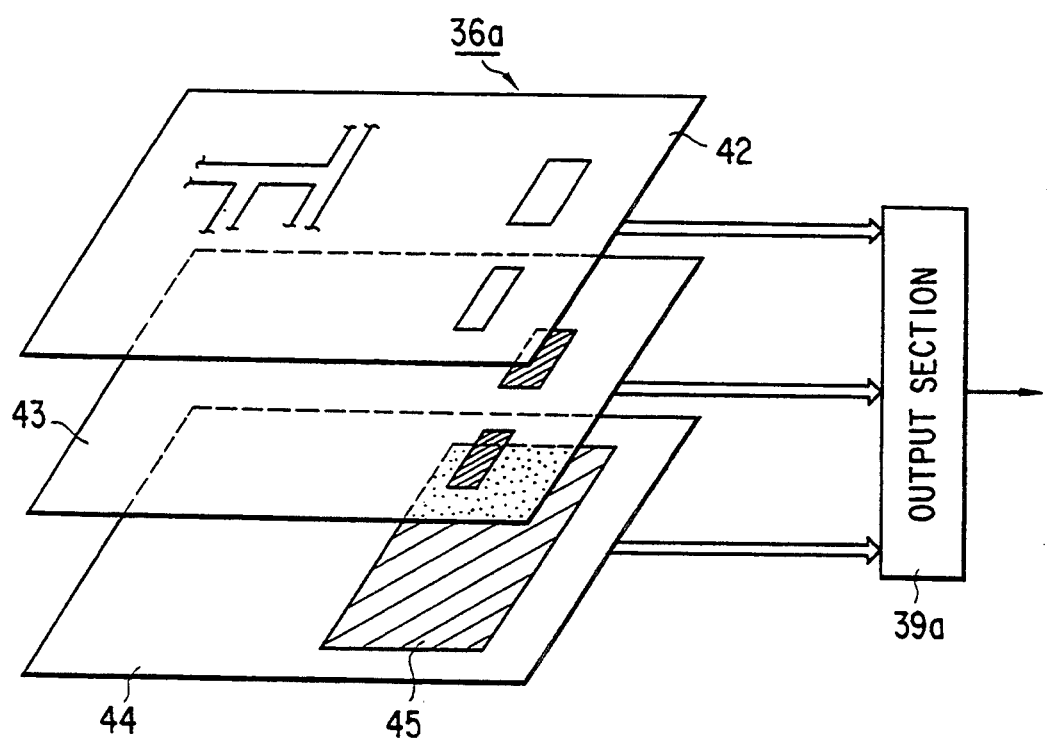
F I G. 9

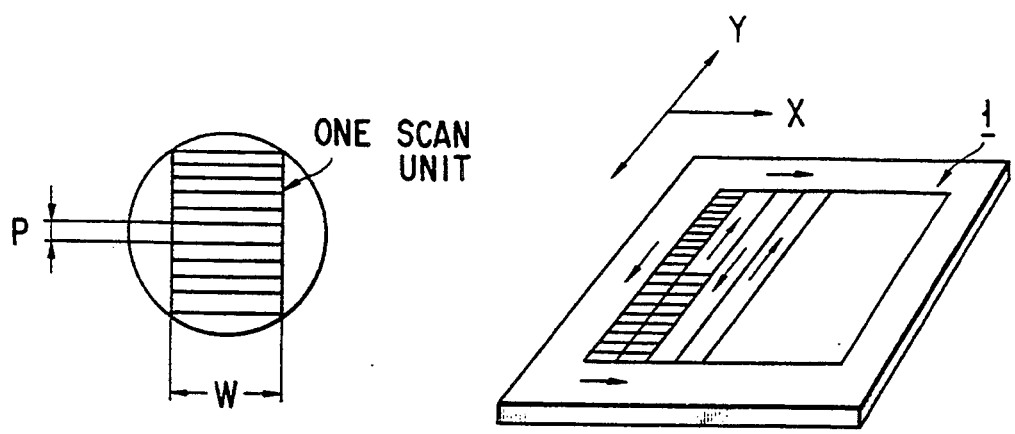
F I G. 12A
(PRIOR ART)
F I G. 12B
(PRIOR ART)
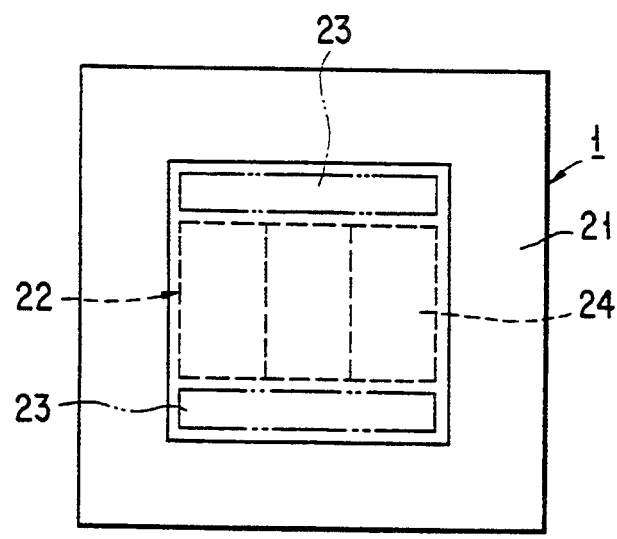
F I G. 13
(PRIOR ART)

PATTERN DEFECTS INSPECTION SYSTEM

BACKGROUND OF THE INVENTION

1. Field of the Invention

The present invention relates to a pattern defects inspection system which utilizes graphic data processing to detect the presence/absence of pattern defects in a sample (e.g., a reticle) on which a pattern, e.g., a photomask used in the process of manufacturing a semiconductor integrated circuit (LSI) or an LCD is formed.

2. Description of the Related Art

In general, in the process of manufacturing an LSI or an LCD, one of the main causes for a decrease in yield is the presence of pattern defects in a photomask used in the process. For this reason, some inspection systems for inspecting such pattern defects have been enthusiastically developed and have already been put into practical use.

FIG. 11 shows the arrangement of an inspection apparatus of the system exemplifying the above-mentioned conventional pattern defects inspection system. More specifically, in this system, the pattern formed on a photomask 1 is enlarged by using an optical system such as a microscope. The enlarged pattern is divided into continuous narrow strips, each having a width W of, e.g., about 500 μm, as shown in FIGS. 12A and 12B. Detection of pattern defects is performed by continuously scanning these divided portions. (Note that in practice, a table is continuously moved at intervals of a predetermined length P.)

A photomask 1 is placed on an XYθ table 2. A predetermined pattern (e.g., an F-shaped pattern) formed on the photomask 1 is illuminated by a light source 3. Light transmitted through the photomask 1 is incident on a photodiode array 5 through a magnifying optical system (e.g., a lens) 4. As a result, an optical image of the pattern is formed on the photodiode array 5. The pattern image formed on the photodiode array 5 is photoelectrically converted by the photodiode array 5. The resultant data is A/D-converted by a sensor circuit 6. Measurement pattern data output from the sensor circuit 6 is supplied to a data comparator 8 together with data output from a positioning circuit 7 and indicating the position of the photomask 1 on the XY8 table 2.

Meanwhile, the pattern design data used to form the pattern on the photomask 1 is read out from a magnetic disk unit 9 and is loaded into a bit pattern generator 11 through a CPU 10. The bit pattern generator 11 converts pattern design data, stored in a magnetic disk (DK) or the like, into binary bit data, and supplies the bit data to the data comparator 8. The data comparator 8 performs predetermined filtering processing with respect to the supplied bit data associated with a graphic pattern so as to convert the data into multivalued (base-n number: plurality of digitized value) data. The reason why this processing is required is that since the measurement pattern data obtained by the sensor circuit 6 has undergone filtering processing based on the resolution characteristics of the magnifying optical system 4, the aperture effect of the photodiode array 5, and the like, the pattern design data needs to be filtered to conform to the data format of the measurement pattern data. The data comparator 8 compares the measurement pattern data with the filtered design data in accordance with a predetermined algorithm, and determines the presence of defects in the pattern if the two data do not coincide with each other.

In order to satisfy the demand for LSIs having higher integration densities, an increase in resolution of an optical transfer unit is demanded. In recent apparatuses, in order to meet such a demand, it is proposed that a phase shift pattern utilizing interference of light be formed on a photomask. More specifically, a pattern formed on the photomask 1 shown in FIG. 13 is roughly divided into a peripheral pattern 21 and a circuit pattern 22. The circuit pattern 22 is further divided into a logic/controller portion 23 and a memory portion 24. It is required that a fine pattern be formed especially on the memory portion 24. It is, therefore, required to form a phase shift pattern on the memory portion 24.

An ordinary photomask is generally obtained by forming a layer having a light-shielding function (the property of shielding light), e.g., a chromium layer on the surface of a glass substrate to have a predetermined pattern (to be referred to as a chromium pattern or a light-shielding pattern hereinafter). A phase shift pattern is generally formed from a transparent material such as $SiO_2$.

Various phase shift structures are formed by different schemes, e.g., the Levenson scheme shown in FIG. 14A, the auxiliary pattern scheme shown in FIG. 14B, the edge emphasis scheme shown in FIG. 14C, the chromium-less scheme shown in FIG. 14D, and the halftone scheme shown in FIG. 14E. Note that a glass substrate 25, a chromium pattern 26, and a phase shift pattern 27 are common portions throughout these drawings.

It is currently required for a pattern defects inspection system to have a function of inspecting pattern defects including phase shift pattern defects with high accuracy. However, the conventional pattern defects inspection system shown in FIG. 11 cannot simultaneously inspect defects in both a chromium pattern and a phase shift pattern which are formed on a sample, e.g., a photomask, together.

As described above, the conventional apparatus of pattern defects inspection system inspects pattern defects by comparing pattern design data used to form a pattern with measurement data obtained by actual measurement. In such an apparatus, however, when pattern defects are to be inspected in a sample such as a photomask having both a chromium pattern and a phase shift pattern, defects in the two patterns cannot be simultaneously inspected. More specifically, since, in an operation of the conventional apparatus, defects in a chromium pattern and those in a phase shift pattern are inspected separately (e.g., at least twice), the time required for such an operation is twice that required for one inspecting operation.

SUMMARY OF THE INVENTION

It is an object of the present invention to provide a pattern defects inspection system which can efficiently and simultaneously inspect pattern defects in two different patterns, i.e., a chromium pattern and a phase shift pattern, formed together on a sample such as a photomask.

In order to achieve the above object, and according to the present invention, there is provided: a pattern defects inspection system comprising a conversion section for radiating light on a sample on which a pattern is formed, receiving an optical image of the pattern, and photoelectrically converting the image, a section for generating measurement pattern data corresponding to the pattern on the basis of a signal obtained by the conversion section, a storage section for storing pattern design data used to form the pattern on the sample, a bit pattern generating section for developing the pattern design data read out from the storage section into bit data, and a determining section for determining the presence/absence of defects in the pattern formed on the sample by comparing the bit data obtained by the bit pattern generating section with the measurement pattern data, wherein the storage section stores light-shielding pattern design data used to form a light-shielding pattern on the sample and phase shift pattern design data used to form a phase shift pattern on the sample according to the same coordinate definition, the two design data being stored to be identifiable, and the bit pattern generating section synthesizes the bit data, obtained by performing bit development of the light-shielding pattern design data, with the bit data, obtained by developing the phase shift pattern design data, and outputs the synthesized bit data.

With the above-described arrangement, even if design data for a light-shielding pattern (e.g., a chromium pattern) and design data for a phase shift pattern are used together, Inspection of pattern defects in the two different patterns can be performed at once. In addition, identifiable information, i.e., information indicating the presence/absence of a phase shift pattern and information indicating the structure, type, and the like of the phase shift pattern, are added to the phase shift pattern design data stored in the storage section. Therefore, even in the process of inspection of pattern defects, the inspection method, the inspection algorithm, and the like can be changed as needed in accordance with an construction from the operator.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a block diagram showing a bit pattern generator as a main portion of a pattern defects inspection system according to the first embodiment of the present invention;

FIGS. 3A and 3B are views for explaining examples of bit data synthesized by the apparatus of the first embodiment;

FIGS. 6A to 6E are views showing the light intensity profiles of beams transmitted through portions having both chromium patterns and phase shift patterns, and portions having only phase shift patterns;

FIGS. 7A to 7E are views showing the light intensity profiles of beams transmitted through portions having only chromium patterns;

FIG. 8 is a block diagram showing the schematic arrangement of a main portion of a pattern defects inspection system according to the second embodiment of the present invention;

FIG. 9 is a view showing the arrangement of a pattern memory section incorporated in a bit pattern generator of the system of the second embodiment;

FIGS. 12A and 12B are views for explaining a method of checking a pattern on a photomask by using the conventional pattern defects inspection system;

FIG. 13 is a view showing a pattern formation region on a conventional photomask.

DETAILED DESCRIPTION OF THE PREFERRED EMBODIMENTS

First Embodiment

Figure 11:
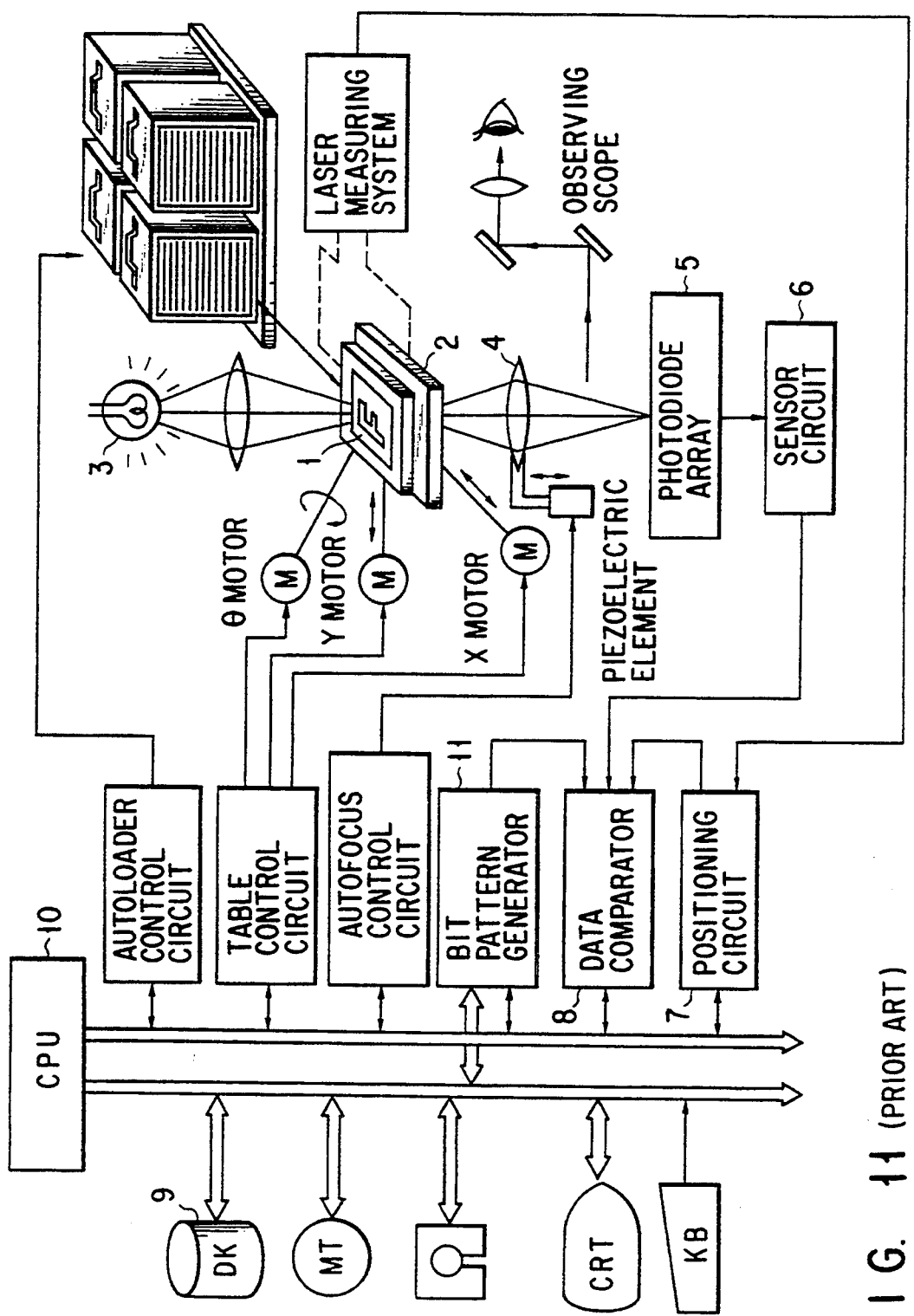
FIG. 11 is a block diagram showing the schematic arrangement of a conventional pattern defects inspection system.

The basic arrangement of a main portion (shown in FIG. 1) of a pattern defects inspection system according to the first embodiment of the present invention is almost the same as that of the main portion of the conventional system (cf. FIG. 11). The same reference numerals in FIG. 1 denote the same parts as in FIG. 11, and a description thereof will be omitted.

Figures 2A, 2B:
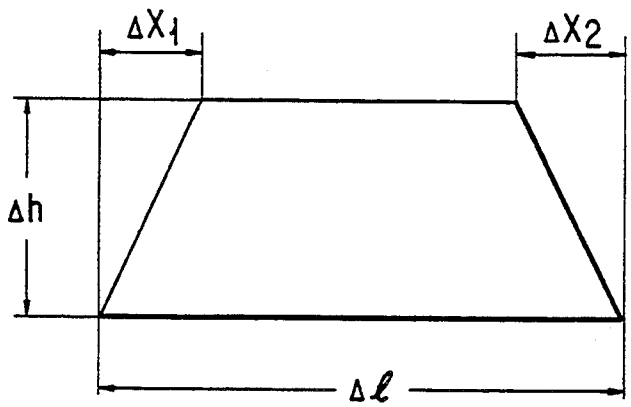
FIGS. 2A and 2B are views respectively showing a graphic pattern stored in a magnetic disk unit of the system and an example of the graphic pattern data.
Figures 4A, 4B:
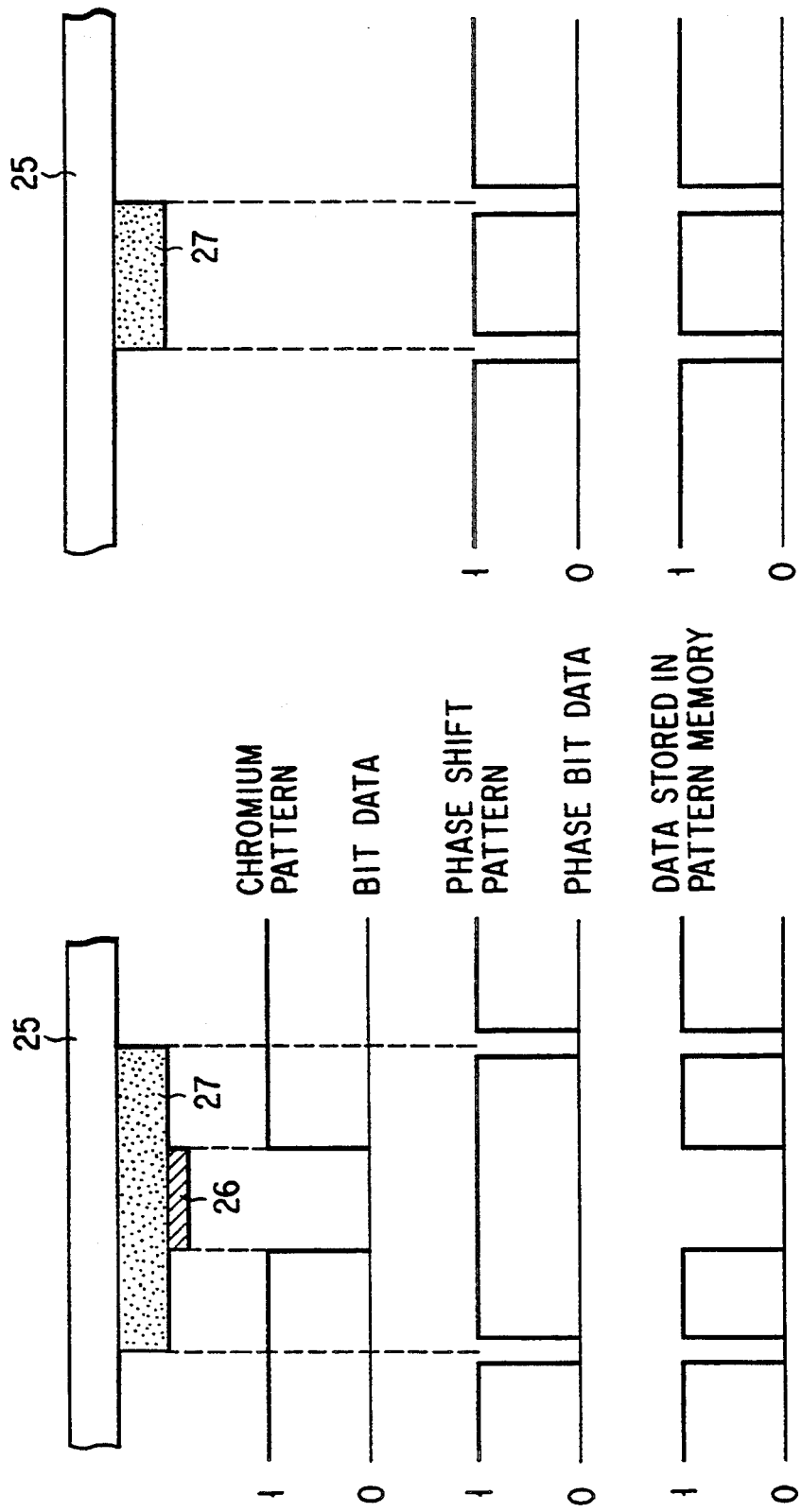
FIGS. 4A and 4B are views for explaining other examples of bit data synthesized by the apparatus of the first embodiment.

The inspection system of the embodiment is different from the conventional system in the structure of pattern design data stored in a magnetic disk unit 9 and the internal arrangement of a bit pattern generator 31. Pattern design data used to form a chromium pattern 26 and a phase shift pattern 27 on a photomask 1 (FIGS. 14A to 14E) is stored in the magnetic disk unit 9 according to the same coordinate definition. More specifically, as shown in FIG. 2A, this pattern design data is represented by a trapezoid as a basic graphic pattern, for example, having a base $\Delta l$, a height $\Delta h$, and offset amounts $\Delta \times 1$ and $\Delta \times 2$. "Identification data" defining the presence/absence or type of a phase shift pattern and "attribute data" designating the operation mode of the bit pattern generator 31 are added to the head of graphic pattern data representing the phase shift pattern 27. On the basis of these data, inspection algorithms respectively required when an inspection target includes only chromium patterns 26, when an inspection target includes only phase shift patterns 27, and when an inspection target includes both patterns, and set values required for these types of inspection are arbitrarily selected and changed in accordance with the designation of an operator or automatically selected and changed in accordance with a predetermined rule. Selection of an algorithm required for this inspection or changing of various set values is performed by the bit pattern generator 31 for developing pattern design data into bit data required for the inspection, control software, and the like.

As shown in FIG. 1, the bit pattern generator 31 temporarily stores pattern design data (i.e., graphic pattern data), supplied from the magnetic disk unit 9, in a memory section 32. This graphic pattern data is transferred for each area to be referred to as a cell having a range suitable for processing. The graphic pattern is then supplied from the memory section 32 to a graphic pattern interpreting section 33. In the section 33, the contents of the graphic pattern are interpreted (e.g., analyzed). If it is determined by this analysis that graphic pattern data associated with a chromium pattern 26 is included in the graphic pattern, the graphic pattern data associated with the chromium pattern 26 is supplied to an oblique line generating section 34. The oblique line generating section 34 generates predetermined oblique lines only when oblique line data (e.g., data representing the oblique lines of a trapezoid) is included in the graphic pattern data. The graphic pattern data is developed into bit data by a subsequent bit development section 35. The bit data obtained by the bit development section 35 is temporarily stored in a subsequent pattern memory section 36. For example, the bit data is then ORed with data supplied from a phase bit development section 37 and a contour bit generating section 38 (both of which will be described later). The resultant data is supplied to an output section 39.

If graphic pattern data associated with a phase shift pattern 27 is included in the graphic pattern data supplied to the graphic pattern interpreting section 33, the graphic pattern data associated with the phase shift pattern 27 is supplied to the phase bit development section 37 to be developed into phase bit data, as indicated by the broken line shown in FIG. 1. As described above, the data supplied to the phase bit development section 37 includes information indicating a phase shift pattern, information indicating the type of the phase shift pattern, and the like. The phase bit data obtained by the phase bit development section 37 is sent to the subsequent contour bit generating section 38. The contour bit generating section 38 is arranged for the following reasons. When various types of phase shift patterns 27 (cf. FIGS. 14A to 14E) are to be processed, the light intensity profiles shown in FIGS. 6A to 6E are respectively observed on the photodiode array 5 side. When only chromium patterns 26 are present, the light intensity profiles shown in FIGS. 7A to 7E are obtained. When phase shift patterns 27 are present, the obtained light intensity profiles are apparently different from these profiles. Especially with respect to graphic pattern data associated with a phase shift pattern 27 whose light intensity profile greatly changes at its contour portions, as shown in FIGS. 6C and 6D, it is preferable to generate phase bit data by extracting only contour data in accordance with this light intensity profile in order to accurately identify the pattern. The contour bit generating section 38 is arranged for this purpose. Note that the width of a phase bit indicating a contour of a phase shift pattern 27 generated by the contour bit generating section 38 can be changed as needed.

The phase bit data of the phase shift pattern 27 developed in the above-described manner and the bit data of the chromium pattern 26 are synthesized with each other by an AND circuit and the like. The resultant data is then stored in the pattern memory section 36. The pattern memory section 36 has a predetermined capacity (e.g., 1,024×1,024 bits) large enough to store a bit pattern having a proper area.

Conversion of data stored in the pattern memory section 36 is performed in accordance with the type (size and shape) of the phase shift pattern 27, as shown in FIGS. 3A, 3B to FIG. 5. In this embodiment, when a bit (defined as, e.g., "0") indicating a light-shielding portion of chromium pattern design data and a bit (defined as, e.g., "1") indicating a phase shift portion of phase shift pattern design data are on the same coordinates, the value of the bit indicating the light-shielding portion is used. Similarly, when a bit indicating a transparent portion of chromium pattern design data and a bit indicating a phase shift portion of phase shift pattern design data are on the same coordinates, the value of the bit indicating the phase shift portion is used. When a bit group indicating a phase shift portion of phase shift pattern design data is present within the area of a bit group indicating a transparent portion of chromium pattern design data, the value of a contour bit (defined as, e.g., "0") generated by the contour bit generating section 38 is used. In this manner, corresponding data are generated. Thereafter, these data are synthesized by an AND circuit and the result is stored in the pattern memory section 36. The bit data stored in the pattern memory section 36 is supplied to a comparator (not shown) having a filter through the output section 39.

Figure 14A:
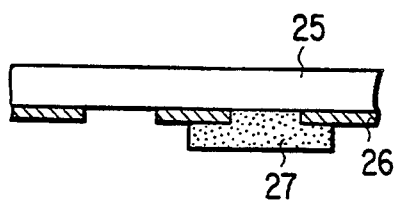
FIGS. 14A to 14E are sectional views showing the structures of phase shift samples based on various conventional schemes.
Figure 14B:
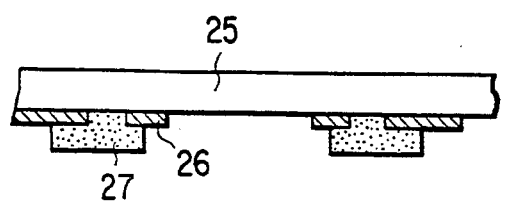
Figure 14C:
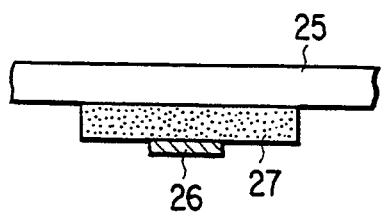
Figure 14D:
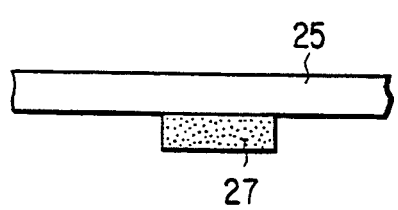

With the above-described arrangement, for example, as shown in FIG. 14C, the following operation is performed with respect to a portion having both a phase shift pattern 27 based on the edge emphasis scheme and an ordinary chromium pattern 26.

First, pattern design data corresponding to the chromium pattern 26 and the phase shift pattern 27 is read out from the magnetic disk unit 9. The read pattern design data (i.e., graphic pattern data) is developed into the bit data of the chromium pattern 26 and the phase bit data, (obtained by extracting only the contour portions of the phase shift pattern 27), by the following components of the bit pattern generator 31: the graphic pattern interpreting section 33, the oblique line generating section 34, the bit development section 35, the phase bit development section 37, and the contour bit generating section 38. After these developed data are generated according to the abovedescribed method (e.g., conversion rule), they are synthesized by, e.g., an AND circuit. The resultant data is then stored in the pattern memory section 36 according to the data format shown in FIG. 4A.

The following processing is performed with respect to a laminated port,on, of each of the laminated structures based on the Levenson scheme and the auxiliary pattern scheme respectively shown in FIGS. 14A and 14B, in which a phase shift pattern or patterns 27 and ordinary chromium patterns 26 are formed together. Similar to the above-described case, in this case, read pattern design data (i.e., graphic pattern data) is developed into the bit data of the chromium patterns 26 and the phase bit data, obtained by extracting only the contour portions of the phase shift pattern or patterns 27, by the following components of the bit pattern generator 31: the graphic pattern interpreting section 33, the oblique line generating section 34, the bit development section 35, the phase bit development section 37, and the contour bit generating section 38. After these developed data are generated according to the abovedescribed method (e.g., conversion rule), they are synthesized by, e.g., an AND circuit. The respective resultant data are then stored in the pattern memory section 36 according to the data formats shown in FIG. 3A and 3B.

Figure 5:
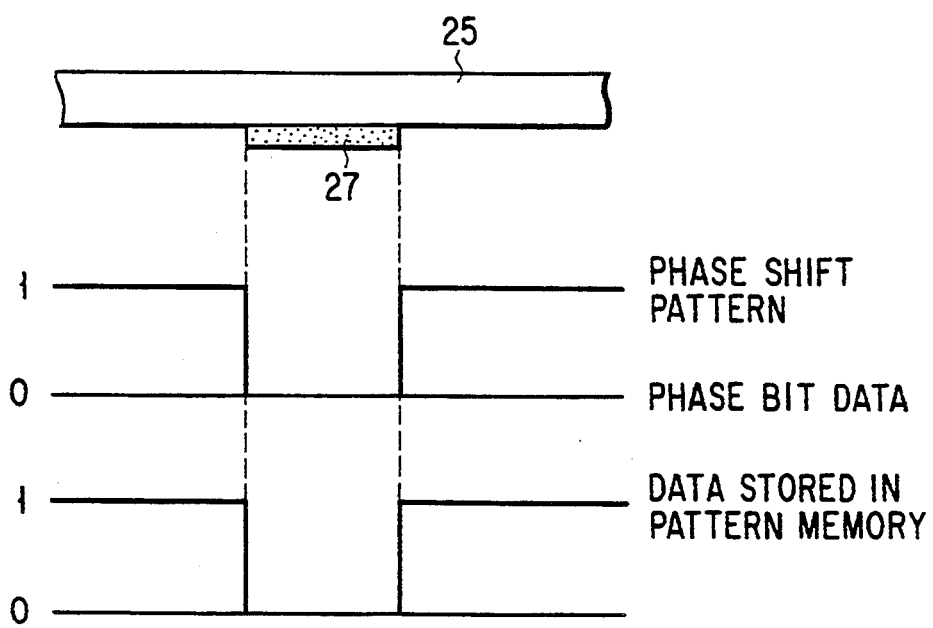
FIG. 5 is a view for explaining bit data synthesized by the system of the first embodiment.
Figure 14E:
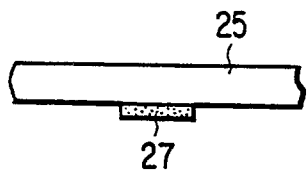

Similar processing is performed with respect to a portion of the laminated structure based on the halftone scheme shown in FIG. 14E, in which a phase shift pattern 27 is present. The phase bit data of the developed phase shift pattern 27 is stored in the pattern memory section 36 according to the above-described method (e.g., conversion rule), as shown in FIG. 5.

The bit data stored in the pattern memory section 36 in the above-described manner is supplied to the filter of the comparator (not shown) through the output section 39. In the comparator, the bit data is compared with measurement pa±tern data obtained from the target pattern. By a proper setting of the filter in accordance with an inspection target, defects in the chromium pattern 26 and in the phase shift pattern 27 can be clearly recognized. Therefore, the above-mentioned different types of patterns can be inspected at once.

In the first embodiment described above, the phase bit development section having the oblique line generating function is arranged in one bit pattern generator to develop design data for a phase shift pattern into phase bit data. However, for example, a plurality of bit pattern generators 31 may be arranged in parallel to separately process pattern design data for a chromium pattern and pattern design data for a phase shift pattern, thus developing them into bit pattern data. Thereafter, the respective multi-valued data is synthesized (by, e.g., an AND circuit). The resultant data may be read out from the pattern memory section 36 by the output section 39 to be supplied, as data on the same coordinates, to the comparator (not shown).

Second Embodiment

FIG. 8 shows the detailed arrangement of a main portion, i.e., a bit pattern generator 31a, of a pattern defects detecting inspection system to the second embodiment of the present invention.

In this embodiment, chromium pattern design data and phase shift pattern design data are respectively stored, as binary data and multi-valued data, in a magnetic disk unit 9 in advance. In order to store multivalued (binary or more) bit data, a pattern memory section 36a has a storage capacity obtained by the following equation:

*storage capacity=(length of bits/pixel count)×pattern area bit count*

In this case, halftone data is intermediate signal data of a multi-gradation system, which cannot be expressed by binary data (0 or 1). Such halftone data is processed by using multi-valued data (i.e., binary value or more) expressed by many bits.

When graphic pattern data for a phase shift pattern 27 is recognized by a graphic pattern interpreting section 33a, the section 33a supplies a multi-value processing designating signal 40 to a bit development section 35a to instruct the section 35a to generate multi-valued bit data corresponding to the above-mentioned halftone data. The number of bits required for multi-value processing is included in the data interpreted by the graphic pattern interpreting section 33a, or may be designated by an operator input from a console CRT 41. In addition, the allowable range of multi-valued data including a binary value or more is determined by the light intensity profile shown in FIG. 7A, which corresponds to intermediate values between the values based on a chromium pattern 26 and a glass substrate 25. In addition, data exceeding the allowable range can also be expressed.

In order to ensure data coexistence with chromium patterns 26, the pattern memory section 36a is separated into a binary bit pattern plane 42 for storing the bit data of chromium patterns 26, and a multi-valued (binary value or more) bit pattern plane 43 for storing the bit data of phase shift patterns 27, as shown in FIG. 9. The bit data stored in these two bit pattern planes are synthesized when the are read out by an output section 39a. In addition, the pattern memory section 36a also includes an attribute plane 44 for recognizing whether data on the multi-valued bit pattern plane 43 is a phase bit of a phase shift pattern 27. This arrangement is reflected in operation mode control of the output section 39a and the subsequent operation control. More specifically, when attribute information 45 is set on the attribute plane 44, the output section 39a may synthesize the data associated with a chromium pattern 26 and stored in the binary bit pattern plane 42 with the data associated with a phase shift pattern 27 and stored in the multi-valued (binary value or more) bit pattern plane 43 by calculating, e.g., the logical product therebetween, when the attribute information 45 is not set, the data associated with a chromium pattern 26 and stored in the binary bit pattern plane 42 may be output. With the above-described arrangement, the same effect as that obtained by the first embodiment can be obtained.

Third Embodiment

Figure 10:
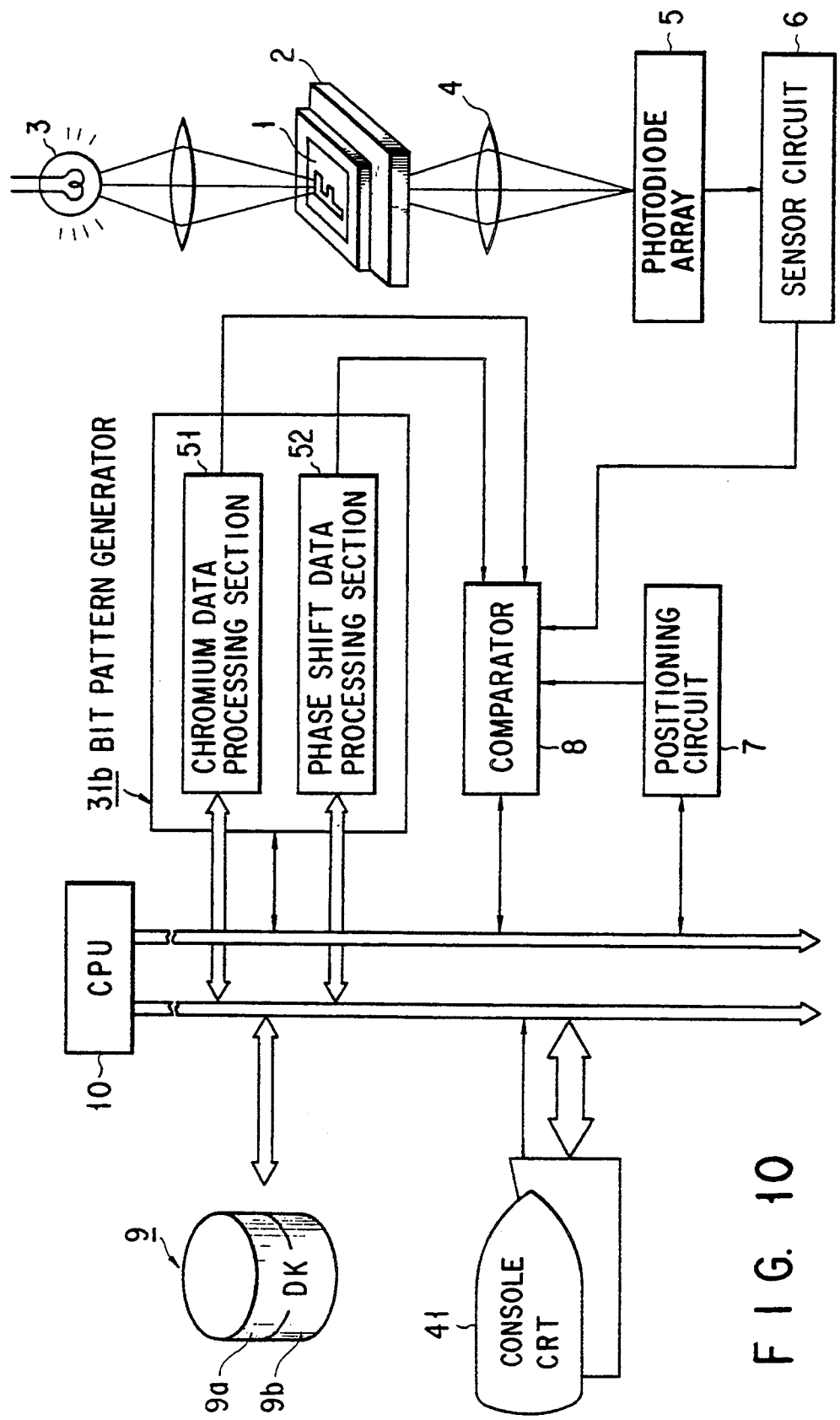
FIG. 10 is a block diagram showing the schematic arrangement of main portion of a pattern defects inspection system according to the third embodiment of the present invention.

FIG. 10 shows the arrangement of an overall pattern defects inspection system according to the third embodiment of the present invention and its main portion, i.e., a bit pattern generator 31b as a characteristic feature of the embodiment.

This embodiment is different from the first and second embodiments described above in that chromium pattern design data and phase shift pattern design data can be separately stored in a plurality of portions (9a and 9b) of a magnetic disk unit 9 according to the same data format (e.g., as multivalued data). The bit pattern generator 31b of the embodiment is characterized by comprising a chromium data processing section 51 and a phase shift data processing section 52 for respectively reading out predetermined data from the portions 9a and 9b of the magnetic disk unit 9, and performing predetermined processing with respect to the data. More specifically, in the first and second embodiments, the graphic pattern interpreting section 33a interprets the format and type (i.e., chromium pattern design data or phase shift pattern design data) of data, and the bit development section 35 performs predetermined development processing on the basis of the interpretation result. In this embodiment, however, since different types of data are independently supplied from the magnetic disk unit 9, the chromium data processing section 51 performs predetermined processing (e.g., the processing described above) with respect to only the chromium pattern design data, and supplies the resultant data to a comparator 8.

Meanwhile, the phase shift data processing section 52 performs predetermined processing (e.g., the processing described above) with respect to only the read phase shift pattern design data, and supplies the resultant data to the comparator 8.

If required, the type of data to be processed may be designated by an construction input by the operator through a console CRT 41, and loading processing of only a desired type of data (e.g., phase shift pattern design data) may be performed in accordance with the instruction.

According to the structure of the embodiment, the following effects can be expected by storing data in units of types or loading data in units of types. The internal arrangement of the bit pattern generator 31b can be simplified. In addition, communication of signals (e.g., a signal which is transmitted when the graphic pattern interpreting section recognizes graphic pattern associated with a phase shift pattern, and instructs the bit development section to generate multivalued (binary value or more) bit data corresponding to halftone data (i.e., the multivalue processing designating signal 40) and the like) between the constituent elements can be omitted. Furthermore, the transmission timing and the like need not be controlled.

Modification

Phase shift pattern design data stored in a storage portion may include information indicating the presence/absence of a phase shift pattern and the structure, type, and the like of the phase shift pattern. These pieces of information are displayed on the screen of a CRT. The operator can change the inspection method, the inspection algorithm, the like to be executed in detection of pattern defects by inputting instructions through a keyboard as needed. By using the data structure including such information, the degree of freedom in application of pattern defects inspection is increased.

Effects of the Invention

As has been described above, according to the respective embodiments described above, the following effects can be obtained:

(1) Defects in a chromium pattern and in a phase shift pattern can be inspected at once by using chromium pattern design data and phase shift pattern design data used to form a pattern on a photomask.

(2) The entire surface of a phase shift mask is not constituted by only a phase shift pattern but has a portion having a very small pattern line width or a portion in which the same pattern is repeated many times. That is, one photomask is manufactured such that a portion constituted by only a chromium pattern and a portion constituted by both a chromium pattern and a phase shift pattern are formed in separate regions. Therefore, the inspection method can be changed in the process of detection of pattern defects depending on whether phase shift pattern data is present in read design data.

(3) Defects in a photomask constituted by only a chromium pattern or in a photomask constituted by only a phase shift pattern can be inspected independently.

(4) By employing the data structure having the information of the presence/absence of a phase shift pattern, the information of the structure and the type of the pattern are included in the phase shift pattern design data. the operator can arbitrarily select an inspection method suitable for the structure of the phase shift pattern, thereby providing a highly practicable pattern defects inspection system which can satisfy the pattern inspection requirements.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A pattern defects inspection system comprising:
conversion means for radiating light on an object to be inspected on which a pattern is formed, said pattern having a light-shielding pattern and a phase shift pattern receiving an optical image of the pattern, and photoelectrically converting the image;
means for generating measurement pattern data corresponding to the pattern on the basis of a signal obtained from said conversion means;
storage means for storing pattern design data used to form the pattern on the object;
bit pattern generating means for developing the pattern design data in said storage means into bit pattern data; and
determining means for determining a presence or absence of defects in the pattern formed on the object by comparing the measurement pattern data with data obtained by performing predetermined filtering processing with respect to the bit pattern data developed by said bit pattern generating means,
wherein said bit pattern generating means further comprising:
graphic pattern interpreting means for recognizing and separating light-shielding pattern design data used to form the light-shielding pattern and phase shift design data used to form the phase shift pattern;
bit pattern development means for developing a corresponding bit pattern of said light-shielding pattern design data and said phase shift design data;
pattern memory means for storing the developed bit pattern data temporarily; and
output means for synthesizing and reading out the bit pattern data to said determining means.

2. The pattern defects inspection system according to claim 1, wherein said phase shift pattern includes a halftone pattern represented by a multi-gradation intermediate signal which cannot be expressed by a binary value based on "0" or "1", said halftone pattern expressed by multi-level data represented by at least two bits, the multi-level data stored in said storage means according to a predetermined conversion rule.

3. The pattern defects inspection system according to claim 2, wherein when said halftone pattern is recognized by said graphic pattern interpreting means, said graphic pattern interpreting means supplies a predetermined multi-level data processing designating signal to said bit pattern development means to for instructing said bit pattern development means to generate multi-level data corresponding to the halftone pattern.

4. The pattern defects inspection system according to claim 1, wherein the light-shielding pattern design data is stored as binary data in said storage means in advance, the phase shift pattern design data is stored, as multi-level data, in said storage means in advance, and the system further comprising pattern memory means for storing the phase shift pattern temporarily, said pattern memory means has a storage capacity large enough to store multi-valued (binary value or more) bit data, the storage capacity being obtained by the following equation:

*storage capacity=(length of bits/pixel count)×pattern area bit count*

5. The pattern defects inspection system according to claim 1, wherein
said bit pattern generating means are arranged in parallel, each identical to said bit pattern generating means to generate bit pattern data by respectively developing the light-shielding pattern design data and pattern design data, and
the respective bit pattern data are synthesized, and the resultant data is output to said determining means by output means through said pattern memory means.

6. The pattern defects inspection system according to claim 1, wherein said storage means includes a plurality of bit pattern planes forming of temporary memory, the bit pattern stored in said bit pattern planes are synthesized when the bit pattern data are output by said output means.

7. The pattern defects inspection system according to claim 6, wherein said storage means further includes an attribute plane for recognizing phase shift bit pattern data of the bit pattern data on said bit pattern, planes and information represented by the attribute plane is reflected in subsequent operation mode control.

8. The pattern defects inspection system according to claim 7, wherein when predetermined attribute information is set on said attribute plane, said output means synthesizes data associated with the light-shielding pattern and stored in said bit pattern planes with data associated with the phase shift pattern and stored in said bit pattern planes, and
when the predetermined attribute information is not set on said attribute plane, the data associated with the light-shielding pattern and stored in said bit pattern planes is output.

9. A pattern defects detecting inspection system comprising:
conversion means for radiating light on an object on which a pattern is formed, receiving an optical image of the pattern, said pattern having a light shielding pattern and a phase shift pattern and for photoelectrically converting the image;
means for generating measurement pattern data corresponding to the pattern on the basis of a signal obtained by said conversion means;
storage means for storing light-shielding pattern design data used to form the light-shielding pattern on the object and phase shift pattern design data used to form the phase shift pattern on the object according to the same coordinates definition, the two design data being stored to be identifiable;
bit pattern generating means for developing the light-shielding pattern design data and the phase shift pattern design data read out from said storage means into bit pattern data individually;
determining means for determining a presence or absence of defects in the pattern formed on the object by comparing the measurement pattern data with data obtained by performing filtering processing with respect to the bit pattern data developed by said bit pattern generating means; and selecting/reading means for selecting data representing the defects as the bit pattern data supplied to said determining means from among the light-shielding pattern design data, the phase shift pattern design data and synthetic data wherein the light-shieldingpattern design data and the phase shift pattern design data are synthesized according to the same coordinate definition, in accordance with the measurement pattern data, and for reading out the selected data from said storage means 10. The system according to claim 9, wherein the phase shift pattern design data stored in said storage means includes information associated with a structure of the phase shift pattern formed by one of the schemes selected from the group consisting of a Levenson, auxiliary pattern, chromium-less, and halftone schemes, and includes information associated with identification of the phase shift pattern.

11. The system according to claim 9, wherein said bit pattern generating means uses a value of a bit indicating a light-shielding portion of the light-shielding pattern design data when the bit indicating the lightshielding portion and a bit indicating a phase shift portion of the phase shift pattern design data are located on the same coordinates, uses a value of a bit indicating a phase shift portion of the phase shift pattern design data when a bit indicating a transparent portion of the light-shielding pattern design data and the bit indicating the phase shift portion are located on the same coordinates, and causes contour bit generating means for generating a contour bit indicating a contour portion of the pattern to generate a contour bit of a bit group indicating said phase shift portion of the phase shift pattern design data when the bit group indicating the phase shift portion is present in a region of a bit group indicating said transparent portion of the light-shielding design data, thereby performing predetermined synthesizing processing with the use of the value of the contour bit.

12. A pattern defects inspection system comprising:
conversion means for radiating light on an object to be inspected on which a pattern is formed, said pattern having a light-shielding pattern and a phase shift pattern, for receiving an optical image of the pattern, and for photoelectrically converting the image;
means for generating measurement pattern data corresponding to the pattern on the basis of a signal obtained from said conversion means;
storage means for storing pattern design data used to form the pattern on the object;
bit pattern generating means for developing the pattern design data read out from said storage means into bit pattern data; and
determining means for determining the presence or absence of defects in the pattern formed on the object by comparing the measurement pattern data with data obtained by performing predetermined filtering processing with respect to the bit pattern data developed by said bit pattern generating means,
wherein said storage means stores light-shielding pattern design data used to form the light-shielding pattern on the object and phase shift pattern design data used to form the phase shift pattern on the object according to the same coordinates definition,
said bit pattern generating means is constituted by light-shielding pattern bit development means for developing the light-shielding pattern design data, used to form the light-shielding pattern on the object, into bit data, and phase shift pattern bit development means for developing the phase shift pattern design data, used to form the phase shift pattern on the object, into bit data, and the bit data, developed by developing the light-shielding pattern design data using said light-shielding pattern bit development means, and the bit data, developed by developing the phase shift pattern design data using said phase shift pattern bit development means, are output to said determining means according to the same coordinates definition.

13. The pattern defects inspection system according to claim 12, wherein the light-shielding pattern design data and the phase shift pattern design data are separately stored in a first storage area and a second storage area as different storage portions of said storage means according to the same multi-level data format.

14. The pattern defects inspection system according to claim 13, wherein said bit pattern generating means is constituted by light-shielding data processing means and phase shift data processing means for independently reading out predetermined data selectively from said first storage area or said second storage area and performing predetermined processing with respect to the read data.

15. The pattern defects inspection system according to claim 14, wherein said pattern design data stored in the storage means including information representing the light-shielding pattern design data or the phase shift pattern design data of the data and indicating a structure of the phase pattern design data, and said bit pattern generating means performs predetermined development processing on the basis of the information included in the pattern design data in advance.

16. The pattern defects inspection system according to claim 14, wherein said storage means further comprises light-shielding data processing means for, performing predetermined processing with respect to only the light-shielding pattern design data, and supplying the processing result to said comparing means, and phase shift data processing means for performing predetermined processing with respect to only supplied the phase shift pattern design data, and supplying the processing result to said comparing means.

17. The pattern defects inspection system according to claim 12, wherein the phase shift pattern design data has a data structure which further includes identification information indicating a presence or absence of said phase shift pattern design data and a structure of the phase shift pattern.

18. The pattern defects inspection system according to claim 17, wherein the identification information is displayed on a screen of a display means, and an inspection method and an inspection algorithm can be selectively designated by a key input means on the basis of the identification information.

* * * * *